US008299788B2

(12) United States Patent
Wheaton

(10) Patent No.: US 8,299,788 B2
(45) Date of Patent: Oct. 30, 2012

(54) MRI USING HYBRID IMAGE

(75) Inventor: Andrew J. Wheaton, Shaker Heights, OH (US)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 285 days.

(21) Appl. No.: 12/861,254

(22) Filed: Aug. 23, 2010

(65) Prior Publication Data

US 2012/0046541 A1    Feb. 23, 2012

(51) Int. Cl.
*G01V 3/00* (2006.01)
(52) U.S. Cl. .................................. 324/307; 324/309
(58) Field of Classification Search .......... 324/300–322; 600/407–445; 705/2–4; 606/155
See application file for complete search history.

(56) References Cited

U.S. PATENT DOCUMENTS

| 6,801,800 | B2 | 10/2004 | Miyazaki et al. | |
| 8,163,003 | B2 * | 4/2012 | Boyden et al. | 623/1.13 |
| 2008/0172073 | A1 * | 7/2008 | Boyden et al. | 606/155 |
| 2009/0261825 | A1 | 10/2009 | Duerk et al. | |

FOREIGN PATENT DOCUMENTS

JP    2003-70766 A    3/2003
JP    2004-329614 A    11/2004

OTHER PUBLICATIONS

Fan, et al., "3D Noncontrast MR Angiography of the Distal Lower Extremities Using Flow-Sensitive Dephasing (FSD)-Prepared Balanced SSFP," *Magnetic Resonance in Medicine*, vol. 62, pp. 1523-1532 (2009).
Fan, et al., "3D Non-Contrast-Enhanced MRA Using Flow-Sensitive Dephasing (FSD) Prepared Balanced SSFP: Identification of the Optimal First-Order Gradient Moment," p. 1410, 17$^{th}$ Annual Scientific Meeting and Exhibition of the International Society of Magnetic Resonance in Medicine, Stockholm, Sweden, (May 2-5, 2010).
Fan, et al., "Carotid Arterial Wall MRI at 3T Using 3D Variable-Flip-Angle Turbo Spin-Echo (TSE) with Flow-Sensitive Dephasing (FSD)," *Journal of Magnetic Resonance Imaging*, vol. 31, pp. 645-654 (2010).
Fan, et al., "Non-Contrast-Enhanced Hand MRA Using Multi-directional Flow-Sensitive Dephasing," p. 405, 17$^{th}$ Annual Scientific Meeting and Exhibition of the International Society of Magnetic Resonance in Medicine, Stockholm, Sweden, (May 2-5, 2010).

(Continued)

*Primary Examiner* — Brij Shrivastav
(74) *Attorney, Agent, or Firm* — Nixon & Vanderhye PC

(57) ABSTRACT

Magnetic resonance images (MRI) are generated by acquiring a plurality of N>2 image data sets for an imaged patient volume using respectively corresponding different data acquisition imaging parameters. At least one hybrid image data set X is generated for the imaged patient volume based on a combination of at least a subset of the plurality of image data sets. If desired, a further subtraction image (e.g., MRA) data set is generated based on a difference between the at least one hybrid image data set and another image data set, and the subtraction image data set, which may, depending upon implementation, optimize flowing fluids such as blood within arteries or veins, CSF, etc within the imaged patent volume, is output for storage or display as an MR image of the imaged patient volume.

22 Claims, 8 Drawing Sheets

OTHER PUBLICATIONS

Guo, et al., "3D Non-Contrast MRA of Lower Extremities Using Balanced SSFP with Flow-Sensitive Dephasing (FSD) at 3T," p. 3786, 17th Annual Scientific Meeting and Exhibition of the International Society of Magnetic Resonance in Medicine, Stockholm, Sweden, (May 2-5, 2010).

Haacke, et al., "Magnetic Resonance Imaging: Physical Principles and Sequence Design," New York: Wiley-Liss, Chapter 23, pp. 673-675 (1999).

Miyazaki, et al., "Peripheral MR Angiography: Separation of Arteries from Veins with Flow-spoiled Gradient Pulses in Electrocardiography-triggered Three-dimensional Half-Fourier Fast Spin-Echo Imaging," *Radiology*, vol. 227, pp. 890-896 (Jun. 2003).

Wang, et al., "Improved Suppression of Plaque-Mimicking Artifacts in Black-Blood Carotid Atherosclerosis Imaging Using a Multislice Motion-Sensitized Driven-Equilibrium (MSDE) Turbo Spin-Echo (TSE) Sequence," *Magnetic Resonance in Medicine*, vol. 58, pp. 973-981 (2007).

* cited by examiner

Improvement of hybrid image over conventional ml = high image. Black pixels represent data removed from final image [mostly veins].

Improvement of hybrid image over conventional ml = mid image. White pixels represent signal improvement.

MRI USING HYBRID IMAGE

FIELD

The subject matter below relates generally to magnetic resonance imaging (MRI) processes. Preferably, the MRI processes described below involve image contrast enhancements that may be achieved without the use of contrast media injections to the patient.

DETAILED DESCRIPTION

Figure 1:
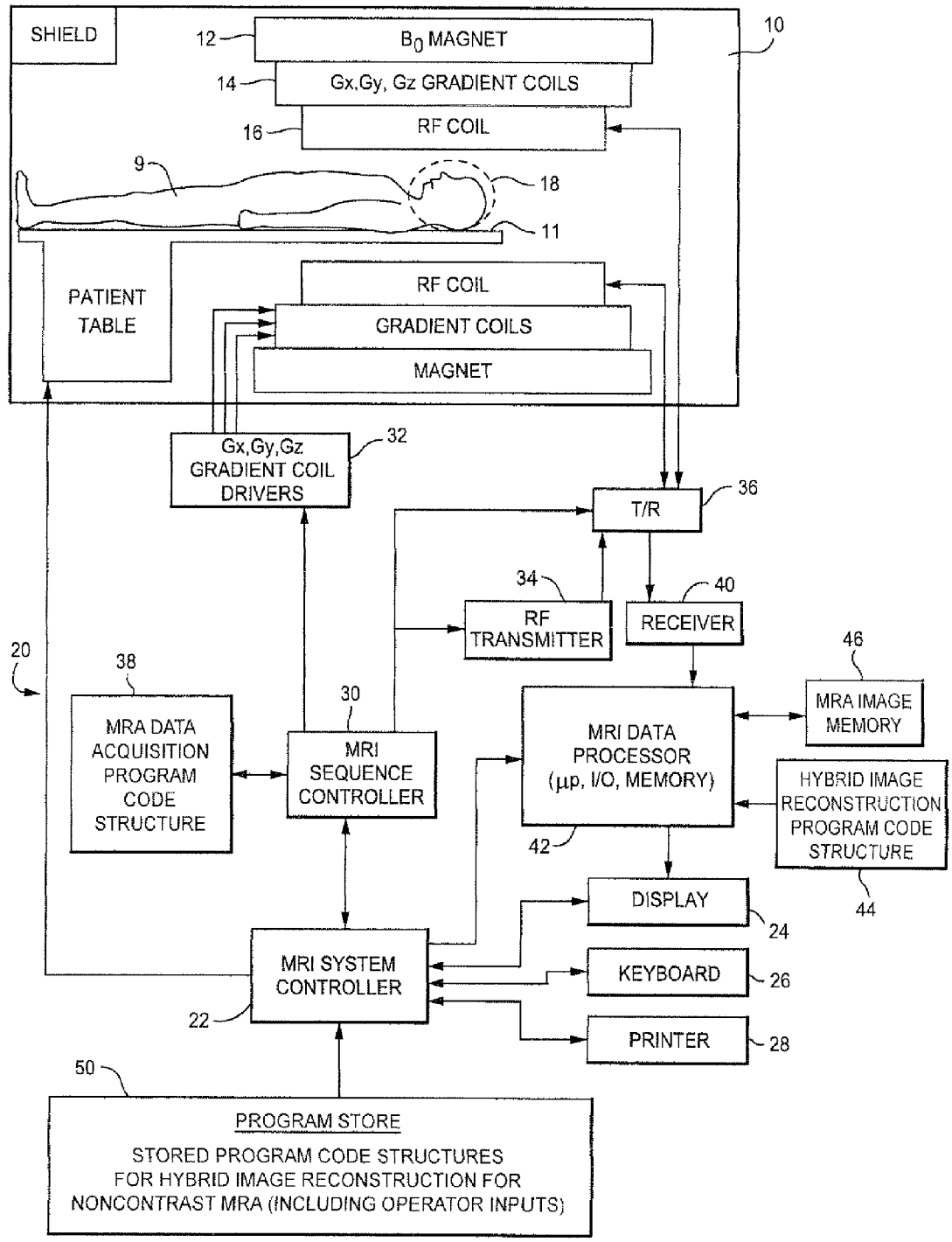
FIG. 1 is a high-level schematic block diagram of an MRI system adapted to acquire and process data for MRA (magnetic resonance angiography) using magnetic resonance using a hybrid image (e.g., a hybrid dark artery (DA) image) based on plural images (e.g., DA images acquired with different imaging parameters)

The MRI system shown in FIG. 1 includes a gantry 10 (shown in schematic cross-section) and various related system components 20 interfaced therewith. At least the gantry 10 is typically located in a shielded room. One MRI system geometry depicted in FIG. 1 includes a substantially coaxial cylindrical arrangement of the static field BO magnet 12, a $G_x$, $G_y$ and $G_z$ gradient coil set 14 and an RF coil assembly 16. Along the horizontal axis of this cylindrical array of elements is an imaging volume 18 shown as substantially encompassing the head of a patient 9 supported by a patient table 11.

An MRI system controller 22 has input/output ports connected to display 24, keyboard 26 and printer 28. As will be appreciated, the display 24 may be of the touch-screen variety so that it provides control inputs as well.

The MRI system controller 22 interfaces with MRI sequence controller 30 which, in turn, controls the $G_x$, $G_y$ and $G_z$ gradient coil drivers 32, as well as the RF transmitter 34 and the transmit/receive switch 36 (if the same RF coil is used for both transmission and reception). The MRI sequence controller 30 includes suitable program code structure 38 for implementing MRA data acquisition sequences using differently valued first-moment m1 flow-spoil dephasing (FSD) magnetic gradient pre-pulses in conjunction with other (e.g., conventional) MRI sequences already available in the repertoire of the MRI sequence controller 30.

The MRI system 20 includes an RF receiver 40 providing input to data processor 42 so as to create processed image data to display 24. The MRI data processor 42 is also configured for access to hybrid image reconstruction program code structure 44 and to MRA image memory 46 (e.g., for storing MRA image data derived from processing in accordance with the exemplary embodiments and the hybrid image reconstruction program code structure 44).

Also illustrated in FIG. 1 is a generalized depiction of an MRI system program store 50 where stored program code structures (e.g., for hybrid image reconstruction for non-contrast MRA, operator inputs to same, etc.) are stored in computer-readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those in the art will appreciate, the FIG. 1 depiction is a very high-level simplified diagram of a typical MRI system with some modifications so as to practice exemplary embodiments to be described hereinbelow. The system components can be divided into different logical collections of "boxes" and typically comprise numerous digital signal processors (DSP), microprocessors, special purpose processing circuits (e.g., for fast ND conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of a hybrid MRA imaging reconstruction process, an array of computer-readable accessible data value storage sites in physical storage media will be transformed from some prior state (e.g., all uniform "zero" values or all "one" values) to a new state wherein the physical states at the physical sites of such an array vary between minimum and maximum values to represent real world physical events and conditions (e.g., the arteries of a patient over an imaging volume space). As those in the art will appreciate, such arrays of stored data values represent and also constitute a physical structure—as does a particular structure of computer control program codes that, when sequentially loaded into instruction registers and executed by one or more CPUs of the MRI system 20, causes a particular sequence of operational states to occur and be transitioned through within the MRI system.

The exemplary embodiments described below provide improved ways to process data acquisitions and/or to generate and display MRA images.

Non-contrast MR angiography (MRA) produces MR images of arterial vasculature without the use of potentially nephrotoxic exogenous contrast material. The purpose of the exemplary embodiments below is to generate non-contrast MRA images with enhanced artery-to-background contrast while avoiding contamination from veins—and/or vice versa (i.e., to generate non-contrast enhanced MR images of veins). N sets of image data acquired with different flow-dephasing gradient moments and/or phases within the cardiac cycle are combined using a hybrid reconstruction algorithm to maximize arterial (or, alternatively, venous) signal while minimizing venous (or, alternatively, arterial) contamination. The process can be operated automatically or semi-automatically with minimal user input. A calibration scan to choose ideal or optimized acquisition parameters is not fundamentally necessary.

A general category of conventional non-contrast MRA techniques is based on the acquisition of two sets of image data: a bright artery (BA) image and a dark artery (DA) image. The DA image data is subtracted from the BA data (on a pixel-by-pixel basis) to produce an MRA image I.

$$I = BA - DA \quad \text{[Equation 1]}$$

The final subtraction image I ideally contains only signal from arterial pixels. The resulting subtraction image data is typically presented in maximum intensity projection (MIP) format for a three dimensional imaged patient volume.

Figure 2:
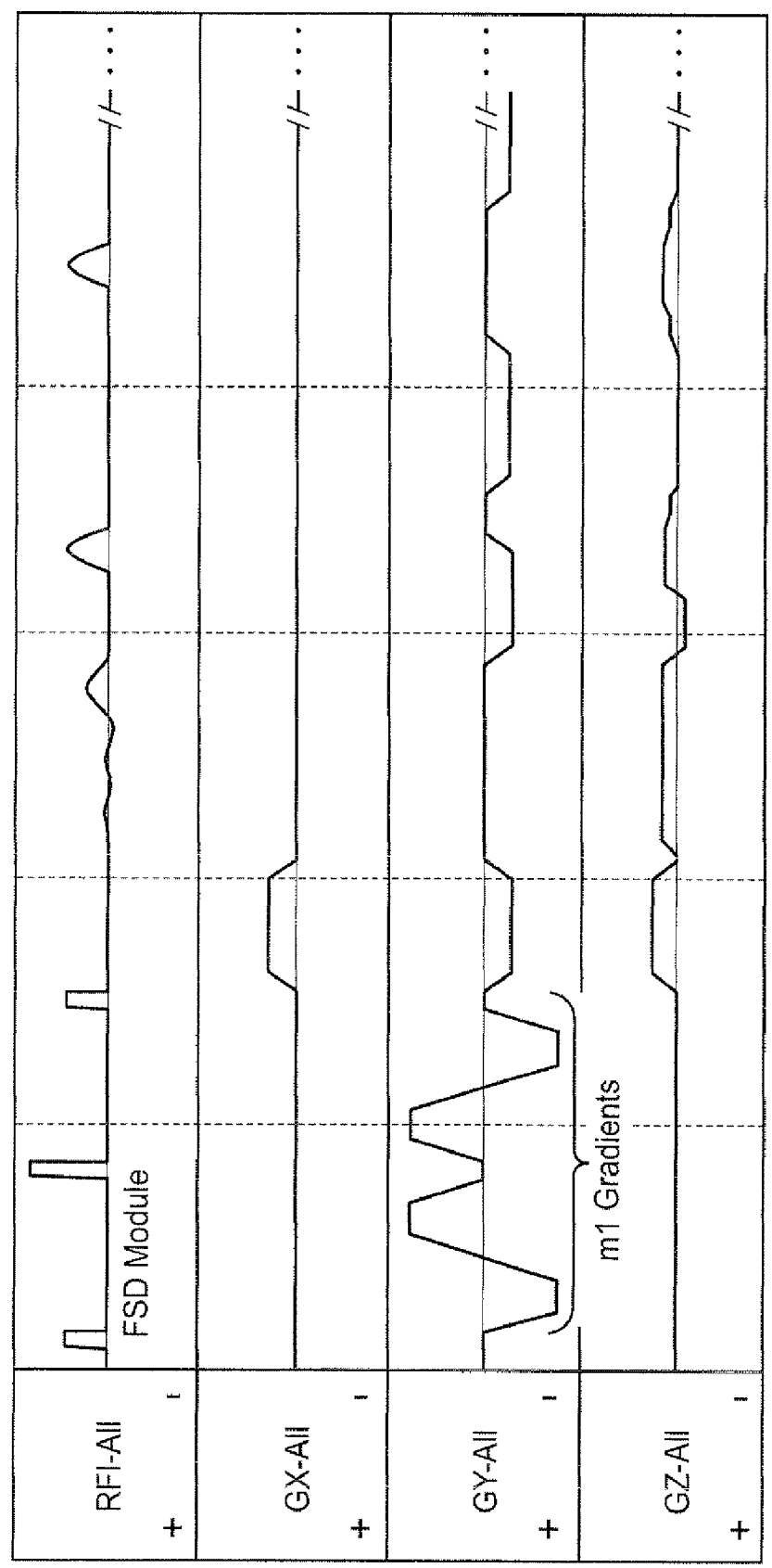
FIG. 2 is a schematic diagram of an exemplary MRI data acquisition sequence utilizing flow-spoiling dephasing (FSD) pre-pulse(s) with non-zero first moment gradient (m1) to dephase flowing spins in the subsequent MRI data acquisition sequence.

A non-contrast MRA technique known as Flow-Spoiled Dephasing (FSD) uses a magnetic gradient pre-pulse module (i.e., as an initial part of a diagnostic MRI acquisition sequence; e.g., see FIG. 2) with a non-zero first moment gradient (m1) to dephase flowing MR spins in the DA acquisition.

Figure 4:
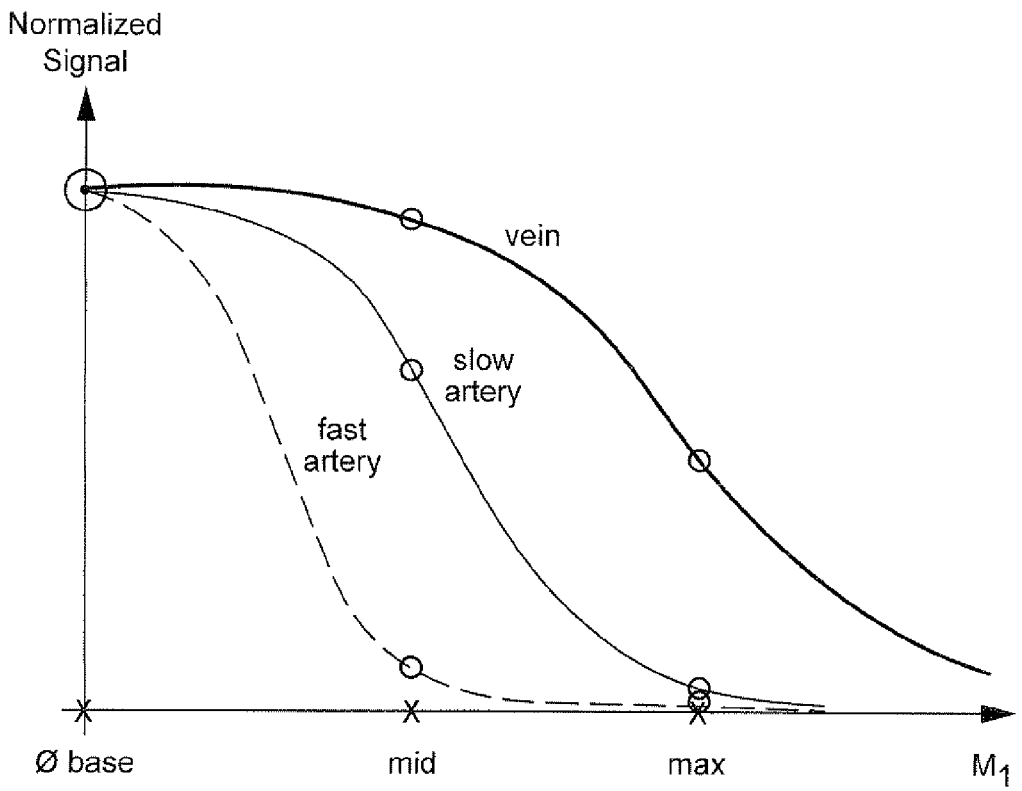
FIG. 4 is a graph depicting typical normalized MRI signal responses emanating from flowing blood in fast arteries, slow arteries and veins for different m1 values.

The total zeroeth moment of the m1 gradients=0. However, their first moment can be non-zero. The combination of null zeroeth moment and non-zero first moment dephases flowing spins, but leaves stationary (background) spins unaffected. The vector orientation of the m1 gradient moment can be manipulated by applying simultaneous m1 gradients on any or all of the gradient channels (x,y,z). Thus the m1 gradient can be designed to preferentially dephase spins flowing parallel to its vector orientation. The signal of the dephased flowing spins is attenuated in the image data. The degree of signal attenuation is non-linearly proportional to the strength of the m1 first moment and flow velocity (FIG. 4). Arteries generally have higher flow velocities and are more strongly influenced by the pulsatile effects of the cardiac cycle compared to veins. Hence, arteries are expected to experience greater signal attenuation than veins, and even more so during systole.

The FSD pre-pulse module can be appended to any conventional MRI diagnostic readout scan sequence (e.g., bSSFP, FASE, etc.). Typically, the readout acquisition is 3D with thin sections to depict small vasculature with sufficient resolution. The FSD pre-pulse module typically is a bipolar 90°-180°-90° RF pulse combination. For the dark artery (DA) scan, m1 gradients are typically set to some calibrated non-zero value. For the bright artery (BA) scan, m1 gradients typically are set to a small or zero amplitude.

Although FSD is used as an example herein, the method to be described can be applied to any non-contrast-enhanced subtraction-based MRI technique designed to depict flowing fluid. This includes techniques like fresh blood imaging (FBI) mentioned herein and other differently named but similar non-contrast enhanced MR angiography (including CSF: cerebral spinal fluid) techniques. Of particular mention is Flow-Spoiled FBI (FS-FBI), a technique which improves FBI by making arterial signal low relative to venous signal using flow-spoiling dephasing gradient pulses during the echo train, not as a pre-pulse as in the case of FSD. This general class of non-contrast-enhanced MRA techniques share the common features of using ECG-gating or PPG-gating and T2 weighted imaging methods as opposed to conventional contrast-enhanced MRA or non-contrast-enhanced MRA (e.g., TOF: Time of Flight) which are typically based on T1-weighted imaging methods. The T2-weighted imaging of the non-contrast enhanced techniques is often performed using a Fast Spin Echo (FSE) pulse sequence to reduce scan time, although this is not a requirement.

FIG. 2 schematically depicts an FSD pulse sequence including a 90°-180°-90° RF pre-pulse module. For plural DA scans, m1 gradients are included (as depicted), but with different magnitudes for different DA image data acquisitions. For the BA scan, m1 gradients are set to zero.

Conventionally, two images are acquired:
a Bright Artery (BA) at diastole with m1=0
a Dark Artery (DA) at systole with m1 ≠0.

Then a final MRA image is created by subtracting the DA image from the BA image on a pixel-by-pixel basis. As noted, this is also similar to the fresh blood imaging (FBI) technique for non-contrast MRA.

Unfortunately, in conventional FSD, the m1 gradient pre-pulse module dephases all flowing MR spins to some degree. The acquired MRI signal attenuation is non-linearly proportional to the velocity of the nuclear spins (FIG. 4). The faster the flow, the more the signal is attenuated. If m1 is too low, arteries will not be fully attenuated in the DA image, especially for slow flow arteries. Hence, these pixel values will be reduced in the final BA-DA subtraction image (e.g., see FIG. 3a, which is a maximum intensity projection (MIP) of a subtraction image with m1 too low). Likewise, if ml is too high, venous flow can also be attenuated in the DA image (e.g., see FIG. 3b, which is a maximum intensity projection (MIP) of a subtraction image with ml too high). Any venous attenuation results in contamination at the venous pixel locations in the final BA-DA subtraction image (see arrows in FIGS. 3a and 3b). Weak arterial signal is highlighted by arrows in FIG. 3a, while venous contamination is highlighted by arrows in FIG. 3b. This problem is especially confounding considering that veins are commonly located directly adjacent to arteries in peripheral patient anatomy.

In conventional FSD, the optimum gradient pre-pulse module first moment ml typically must, therefore, be calibrated to avoid the problems associated with (a) losing arterial signal with m1 too low, or (b) introducing venous contamination with m1 too high. This calibration step can be performed per-experiment by estimating ideal m1 in a sub-portion of the imaging volume by selecting a 2D slice. Alternatively, ideal m1 can be estimated on a population-average basis by performing FSD experiments on a representative cohort in a separate study. Such calibration procedure adds another step to the process and undesirably consumes time. It also adds a potential source of error.

Most importantly, the use of a single ml value can result in sub-optimal vasculature depiction in portions of the imaging volume. If the ideal m1 value is calibrated on a per-experiment basis, it is generally estimated based on a limited portion of the vessels within a 2D slice. This single 2D slice covers only a fraction of the full 3D imaging volume. Since flow rates and pulsatility can be substantially different across the vessels within the imaging volume, ideal ml estimated via this 2D approach can produce sub-optimal results for substantial portions of the vasculature. If ideal m1 is estimated on a population-average basis, not only can it be sub-optimal for portions of the vasculature, it can potentially be sub-optimal for each individual subject.

Now, however, using a hybrid image in processes as described below, it is possible to practice FSD with a final subtraction image I having (a) increased arterial signal and (b) reduced venous contamination. Alternatively, the final subtraction image may not even be needed since the hybrid image itself may suffice as an output MRA image (of enhanced arteries or enhanced veins).

For example, plural (N) data sets (N≧2) are acquired. In general, if a form of FSD is to be practiced, plural DA image sets are acquired at different m1 values. In one example (FIG. 4), N=3 image sets (base, mid, max) are acquired: a base image set with m1=0 (in diastole), a mid-range image set with m1=middle value (in systole), and a maximum image set with m1=a highest value (in systole). The MRI signals emanating from MR blood nuclei for veins, slow-flow arteries and fast-flow arteries are plotted in FIG. 4 as a function of m1. Three image data sets are acquired: base, mid and max (at x-marked positions on the m1 axis). The signals at these selected m1 values for each vessel type are indicated by circles (○) on the signal curves.

The approach herein described uses a hybrid reconstruction algorithm to maximize arterial signal while minimizing venous signal (or vice versa). For example, N (N≧2) image sets may be acquired with some difference in their flow-dephasing moment (m1) and/or phase within the cardiac cycle. For instance, multiple m1 values and/or vector orientations can be used at the same systolic trigger delay time or the same m1 value can be used at multiple trigger delay times. Alternatively, some combination of multiple m1 values, vector orientations, and trigger delay times can be employed. These images are then input into an algorithm that attempts to separate arterial, venous, and background pixels from each other using an a priori expectation of the relative signal for each component based on the known m1 and/or cardiac phase associated with each input data set. The pixel data from each input data set are combined (e.g., using a selective pixel substitution algorithm) to create a hybrid image set. The hybrid combination algorithm is steered by parameters which can either be fixed or adjusted with optional user input. The hybrid image set can be used in a subtraction process (e.g., FSD) to create a final MRA image with optimal arterial signal and minimal venous signal—or the hybrid image itself may be used as the output MRA image.

Figure 5:
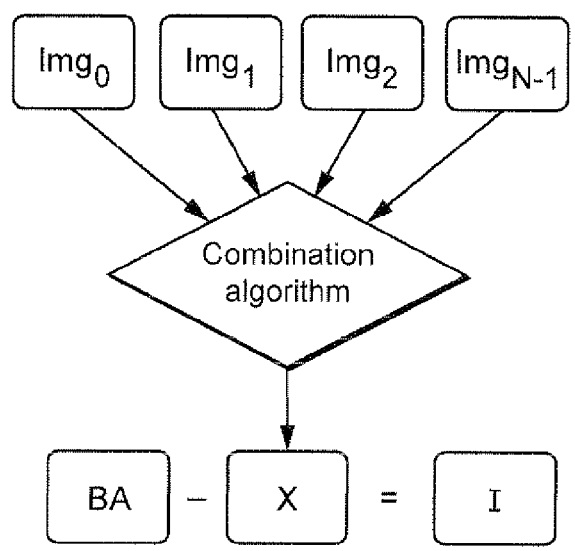
FIG. 5 schematically depicts an exemplary combination algorithm for deriving a hybrid dark artery image X by combining plural dark artery images acquired using different MRI parameters.

Instead of a simple blind subtraction (Equation 1), the pixel data from each image set can be input into a combination algorithm to create a hybrid image set X (FIG. 5). In the combination algorithm, at least two of the pixel data sets are compared against each other to make an intelligent guess as to whether each pixel in a given image data set represents signal emanating from part of an artery, part of a vein, or background. The exemplary output hybrid image data set X can be created by using a pixel value at each X(x,y,z) location (in the hybrid image data set) taken from a selectively chosen from one of the plurality of N different image data sets. This hybrid image data set X can then be used in the usual subtraction formula to create a final improved MRA image I—or, if the hybridization algorithm is appropriately designed, to use the hybrid image data set itself as the final improved MRA image I.

For example, as noted, one may acquire N image data sets (N≧2) at different m1 values such as:
base: m1=0
mid: m1=middle value
max: m1=strong value The resulting N-1 (i.e., two in this example) data sets associated with a non-zero m1 value can then be combined (e.g., by a selective pixel substitution algorithm) into a hybrid image data set X using differences in acquired pixel data values to estimate whether a particular pixel in a particular acquired image belongs to an artery or to a vein. Then a final image I can be calculated using the hybrid image data set X as the DA image data set:

$$I(final)=BA(bright\ artery)-X(DA\ hybrid) \quad [Equation\ 2]$$

Figure 6:
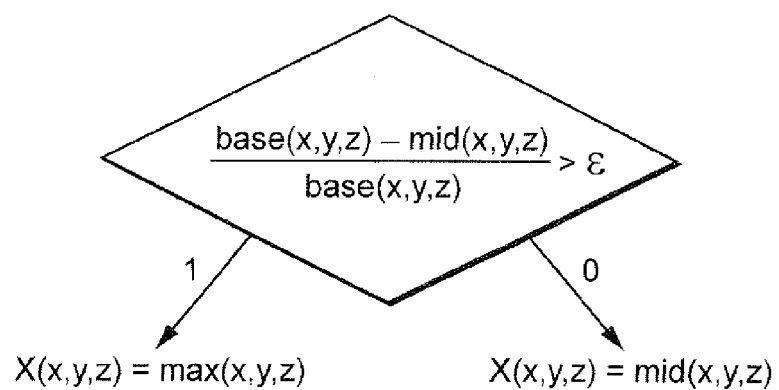
FIG. 6 schematically depicts an exemplary combination algorithm in more detail.

FIG. 5 depicts a possible generalized combination algorithm to create a hybrid image data set X for non-contrast MRA image subtraction. FIG. 6 depicts a more specific example of a combination algorithm for creating a hybrid image data set X. The pixel data at a given location (x,y,z) from all data sets (base, mid, max) is evaluated using the decision algorithm as shown to fill the value of X(x,y,z) in the hybrid image data set X.

As those in the art will recognize, the combination process can take many different forms. In this example with N=3 image sets, the process of FIG. 6 may suffice. A threshold parameter (ε) is used to help decide if a pixel belongs to an artery or to a vein. If the mid-m1 value pixel data is much lower than the base value, it is judged to be an artery (see FIG. 4), so the algorithm fills X(x,y,z) with data from the maximum m1 value image data set at (x,y,z) to maximize signal at this position (x,y,z). If the mid-m1 value pixel data is close to the base value, it is judged to be background or a vein, so the algorithm fills X(x,y,z) with data from the mid-m1 value pixel data set at (x,y,z) to avoid introducing venous contamination. The choice of ε is freely adjustable and/or its value can be fixed for each anatomy based on prior measurements. Alternatively, ε can be adjusted by the user interactively (e.g., in post-processing). Either way, the choice of ε only affects the reconstructed output. Since it does not affect input data, the final decision of ε is not required to be solidified prior to data acquisition. In this manner, a hybrid image X is generated. As will be apparent to those in the art, many different hybridization algorithms/processes may be employed to generate hybrid image X. If the pixel fillings/substitutions are wisely made, the hybrid image X itself may suffice as an output MRA image.

Figure 10:
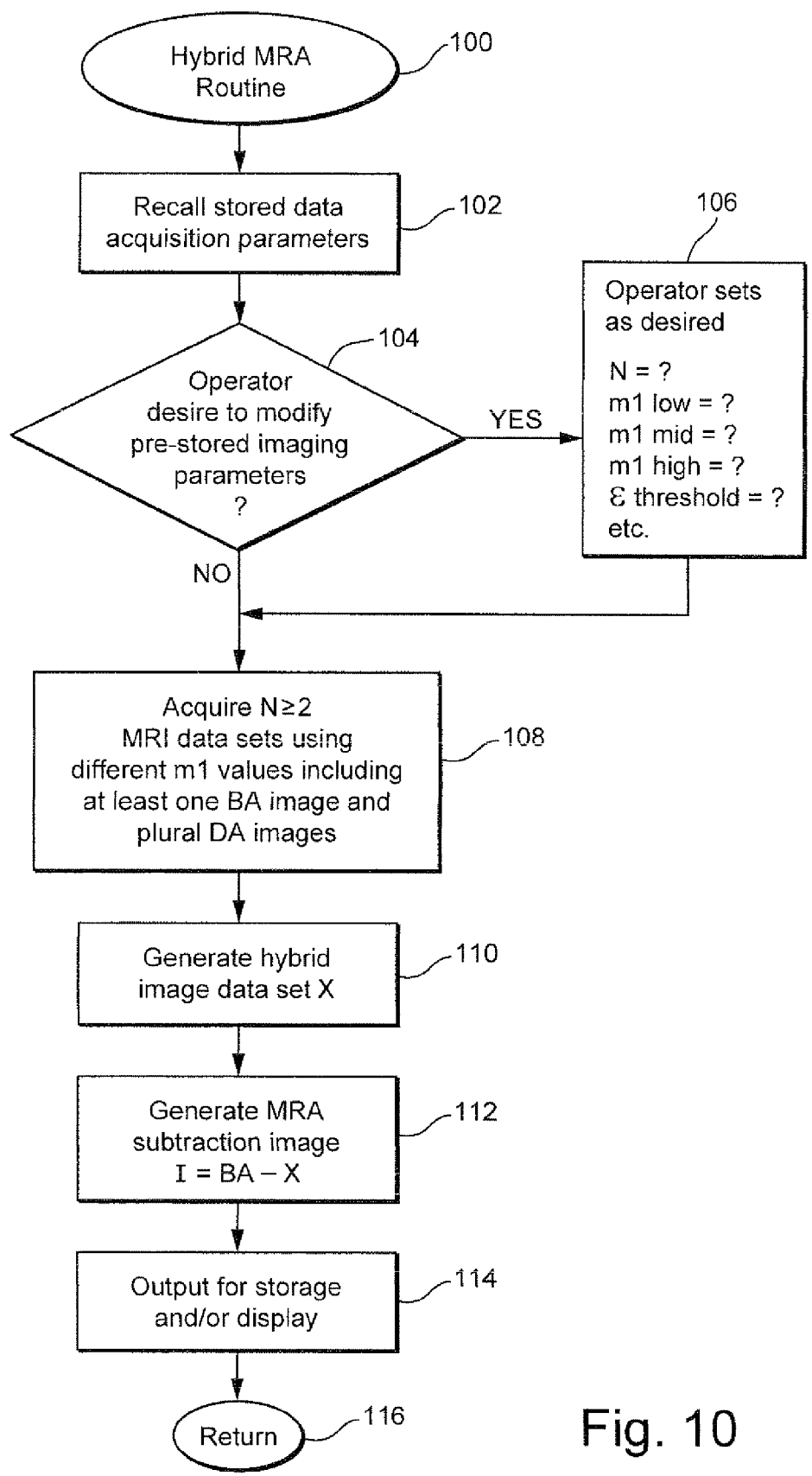
FIG. 10 is a schematic flow chart of exemplary computer program code structure that may be utilized for practicing an exemplary embodiment—including the optional provision of some operator inputs to the process depicted.

A schematic flow chart of exemplary computer program code structure for implementing an exemplary embodiment is depicted at FIG. 10. Here, the hybrid MRA routine is entered at 100 and stored data acquisition parameters as appropriate are recalled from storage at 102. As those in the art will appreciate, other desired initialization processes may also take place at this point.

At decision point 104, an operator is given an option (e.g., via a control display screen/keyboard or touch-sensitive screen or the like) to modify pre-stored imaging parameters if desired. If the option is exercised, then an operator user interface 106 permits the operator to define/modify parameters such as the number of images to be acquired, the low, mid and high values of the m1 parameter, particular value(s) for the threshold parameter, etc. If the option is not exercised, then the pre-stored imaging parameters are utilized instead at step 108 to acquire the N MRI data sets using different m1 values. In this particular exemplary embodiment, such includes at least one BA image and plural DA images (e.g., using different MRI and/or cardiac cycle parameters).

Thereafter, at step 110, a hybrid image data set X is generated (e.g., in accordance with any desired algorithm) and a subtraction MRA image is generated at step 112. That image may then be output for storage and/or display (immediately or later, at an MRI system console or remotely as may be desired) at step 114 before the hybrid MRA routine is exited by return to other program code structures as appropriate at return step 116.

Figure 7:
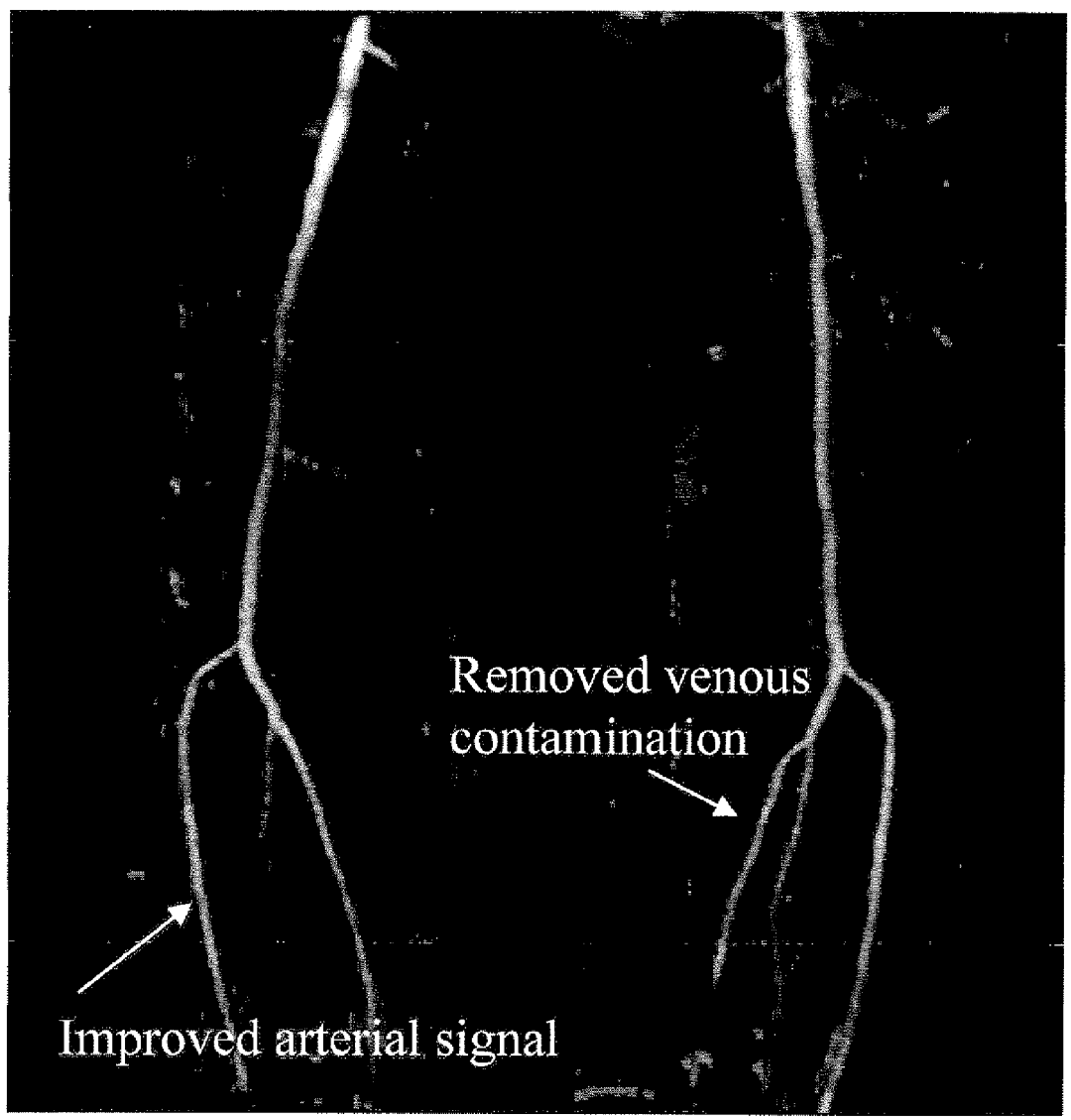
FIG. 7 depicts an MRA image with improved arterial signal.
Figures 8A, 8B:
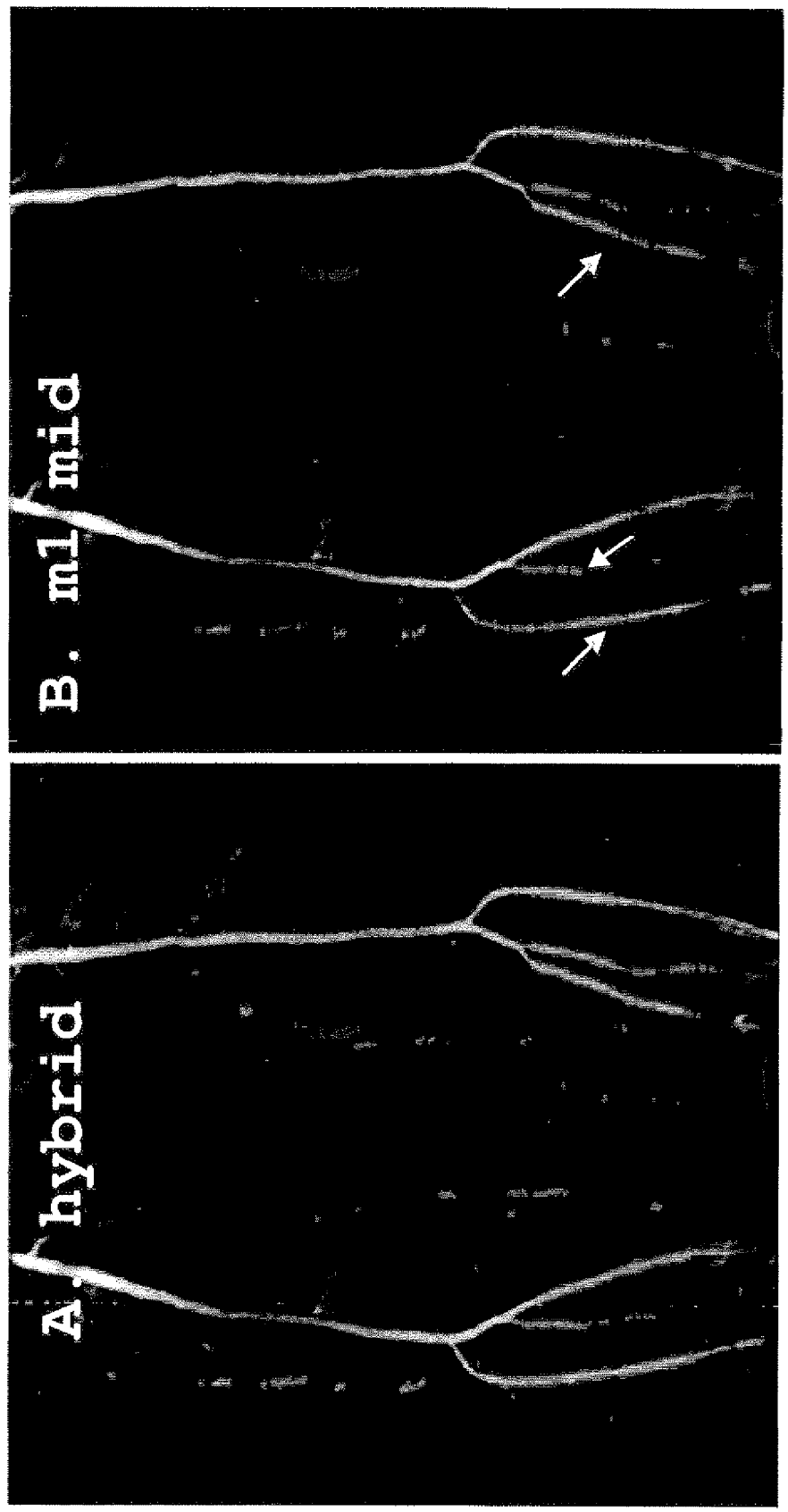
FIGS. 8a-8b depict a hybrid image (FIG. 8a) and one obtained using a mid or intermediate m1 value (FIG. 8b)
Figure 9B:
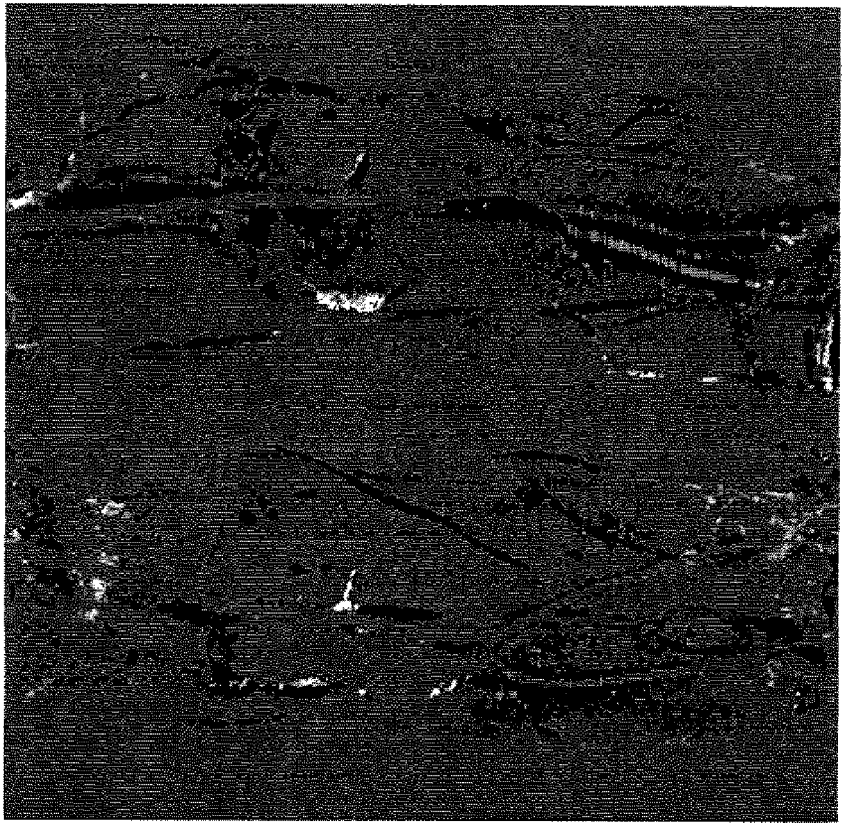
FIGS. 9a-9b depict the improvements exhibited by use of a hybrid image MRA over a conventional MRA image using m1 of a mid or intermediate value as compared to one using a high m1 value.

A principal advantage of this hybridization technique is that it provides MRA image data with strong arterial depiction, even in slow flow arteries, with minimal venous contamination (FIGS. 7, 8*a* and 8*b*). Arterial signal can be potentially enhanced 80-100% (FIG. 9*a*) and venous contamination reduced to almost zero (FIG. 9*b*).

Another advantage of the hybridization technique is that it removes the burden of accurately calibrating m1 for an FSD process. In the conventional FSD approach, the DA scan m1 value must be chosen carefully to make a trade-off between maximizing arterial signal and minimizing venous contamination. In the new hybridization technique, the value of m1=max can be fixed. The choice of m1 for the mid-range data set is simplified; m1 should be large enough to dephase some flow, but not too large to strongly attenuate veins. This relaxed choice of m1 may allow the calibration step to be skipped altogether and improves the robustness of FSD imaging.

Figure 3B:
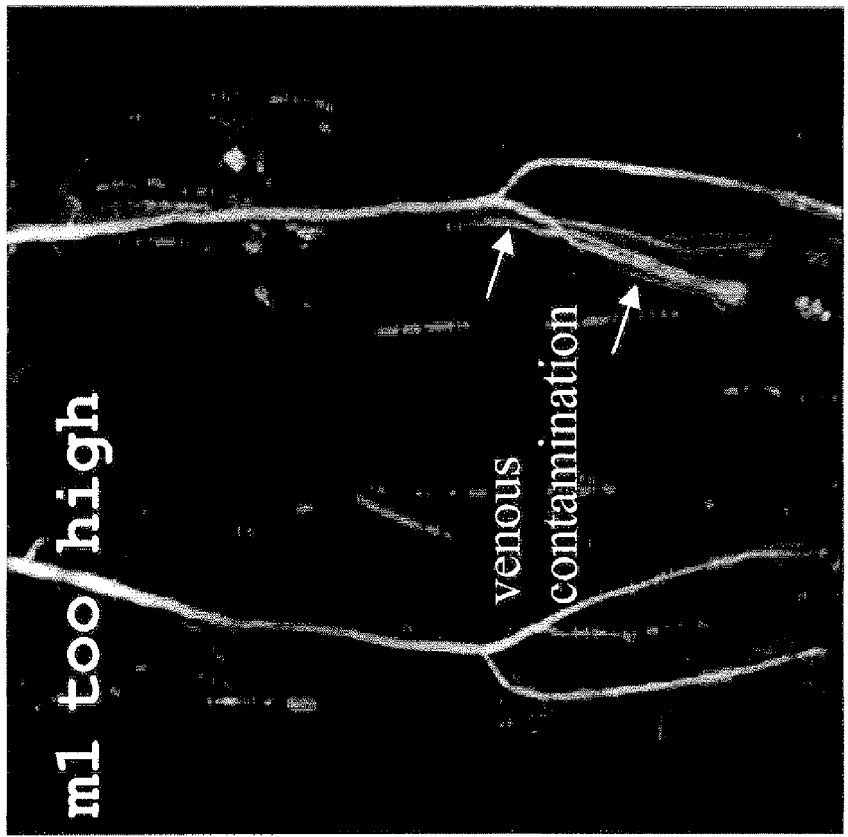
FIGS. 3a-3b depict the consequences of flow-spoiled dephasing (FSD) MRA when the dark artery image is acquired with m1 adjusted too low (FIG. 3a) and too high (FIG. 3b)
Figure 3A:
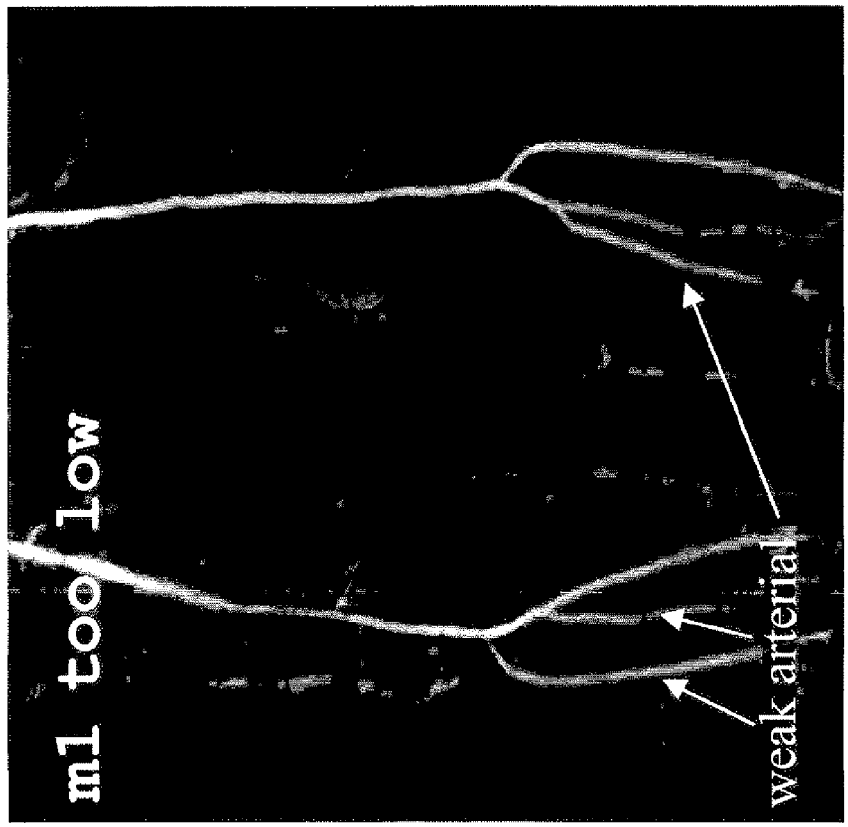
Figure 9A:
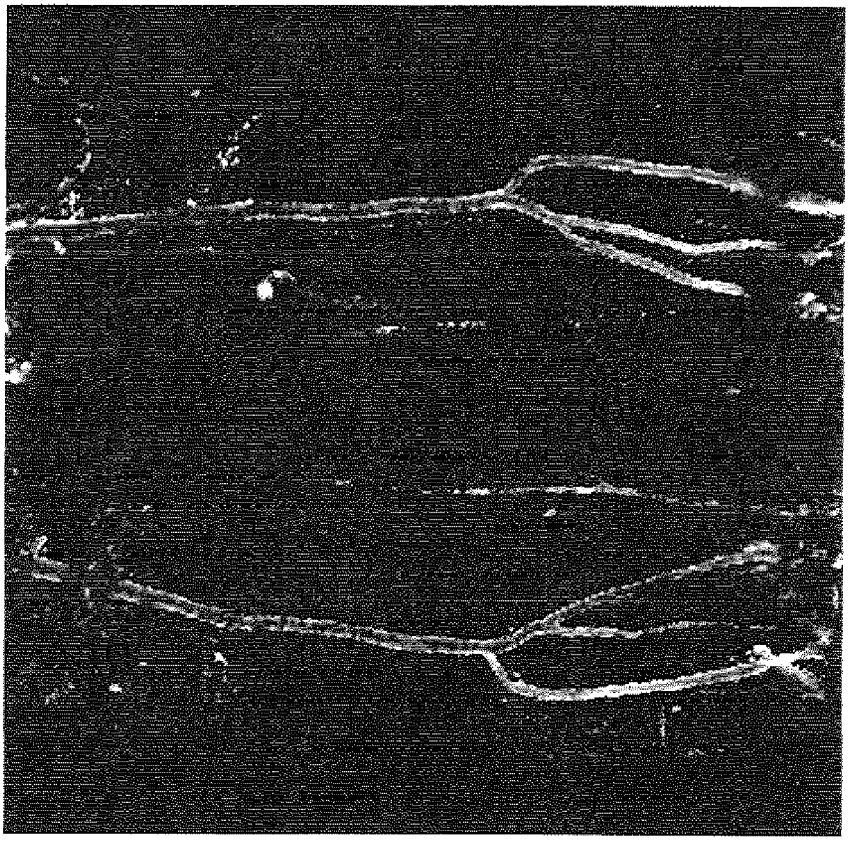

FIG. 8*a* depicts an MIP of a subtraction image produced with the example hybrid method. Arterial signal is increased in distal arteries compared to an MIP image made using only m1=mid data as shown in FIG. 8*b*. FIG. 9*a* depicts the improvement of a hybrid image (FIG. 8*a*) over conventional mid image (FIG. 8*b*). Here, white represents desired signal improvement. FIG. 9*b* depicts improvement of the hybrid image (FIG. 8*a*) over conventional max image (FIG. 3*b*). Here, black pixels depict signal that is desirably excluded from the final image. In both FIGS. 9*a* and 9*b*, gray is neutral (i.e., no change from conventional FSD).

As noted above, the equation of the combination algorithm can be of numerous forms. For example, pixels from each data set can be compared to each other individually. For the above example using N=3, comparisons of base:mid, mid:max and base:max can be performed with three separate threshold parameters. As another example, the arithmetic comparison can be replaced with a fitting function. Since the relationship between signal and m1 can be analytically described by a sinusoid or similar mathematical function, pixel data from each set can be fitted to an analytical function. Like the arithmetic comparison, the resultant fitting parameters can be used to make a decision about the nature of that pixel location (artery, vein or background).

As those in the art will now appreciate, the combination algorithm also can be designed to output the final MRA image set I (e.g., to skip the typically separate subtraction step of BA−X=I). In this case, the selection of pixel values from the plural acquired images is made intelligently so as to include only desired (artery or venous) pixel values in the hybrid image itself.

As will also be understood by those in the art, the process herein described can be applied to any subtraction-based MRA technique. It is not limited to FSD, but can be applied in combination with other techniques such as FS-FBI. In FS-FBI, the flow-dephasing effect is intrinsic to the RF echo train of the fast-spin-echo-based pulse sequence used for data acquisition, not as part of a separate pre-pulse module like FSD. By adjusting the read, phase-encode, or slice spoiling gradient amplitudes following each RF echo of the echo train, the effective m1 flow-dephasing vector amplitude and direction can be controlled. Thus, multiple FS-FBI data sets can be acquired using different m1 dephasing gradients and/or different cardiac phase delays. The multiple data sets can be acquired with different m1 values, different m1 directions, different trigger delays, or any combination thereof. In a similar manner to the FSD example described above, N FS-FBI datasets can be combined to create a hybrid image X and subsequently used in subtraction to create an artery-optimized or vein-optimized image I.

The flowing fluids in the body are not limited to blood, but also include CSF, lymph, bile, pancreatic juice, etc. In general, the process described herein can be used to help separate signal from flowing fluid from other moving fluids and/or background. It does not rely on MR relaxation characteristics of the fluid (e.g., T1, T2, T2*), only its flow characteristics. If the flowing fluid to be isolated has a characteristic flow velocity, flow orientation, and/or relationship to the cardiac or respiratory cycle that are different than those characteristics of the possibly confounding nearby fluid, a set of m1 gradients and trigger delay times can be designed to leverage this difference. These data sets can be processed by the hybrid technique to optimize the depiction of this fluid of interest. Thus, as noted, the process herein described can be used to produce vein-optimized MRA images for venography applications. That is, by modifying the combination algorithm and/or subtraction process, venous signal can be maximized while minimizing arterial signal. As another example, CSF has characteristically slower flow velocity than either arteries or veins. Thus, this fluid characteristic can be leveraged to separate CSF from faster flowing fluids like blood.

Conventional FSD requires only N=2 image sets to be acquired. Thus, there is a (N−2)/2 proportional time savings with the conventional approach. For example, an N=3 experiment with the new hybrid technique takes 50% longer than conventional FSD. However, the calibration scan and calibration data processing, which now can be skipped, costs time. The time for calibration data acquisition and processing can be reasonably estimated to take roughly the same time as a single dataset acquisition (typically two minutes) Thus, an N=3 experiment or hybridization takes roughly the same total time as a conventional FSD experiment.

While certain embodiments of the inventions have been described, these embodiments have been presented by way of example only, and are not intended to limit the scope of the inventions. Indeed, the novel methods and systems described herein may be embodied in a variety of other forms. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A method for generating a magnetic resonance image of fluid, said method comprising:
   using a magnetic resonance imaging (MRI) system gantry to acquire a plurality of N>2 image data sets for an imaged patient volume using respectively corresponding different data acquisition imaging parameters;
   using at least one programmed computer to:
      generate at least one hybrid image data set X for said imaged patient volume based on selective filling of a data set X pixel value at a particular location using pixel values at said particular location found in at least one of at least a subset of said plurality of image data sets; and
      output an image data set that is based on said hybrid image data set X for storage or display as an image of said imaged patient volume.

2. The method of claim 1, wherein said image set emphasizes MRI signals emanating from veins within said patient volume while de-emphasizing MRI signals emanating from arteries within said patient volume, thus providing a vein-optimized venography image.

3. The method of claim 1, wherein said image set emphasizes MRI signals emanating from arteries within said patient volume while de-emphasizing MRI signals emanating from veins within said patient volume, thus providing an artery-optimized arteriographic image.

4. The method of claim 1, wherein:
at least one bright artery image data set BA is generated for said patient volume based on at least one of the acquired image data sets;
at least one hybrid dark artery image data set $DA_x$ is generated for said patient volume based on at least a subset of plural of said acquired image data sets; and
an MRA subtraction image data set is generated by the difference between said BA and $DA_x$ data sets.

5. The method of claim 1, wherein said different data acquisition imaging parameters comprise:
(i) a lowest first-moment m1 flow-spoiled dephasing magnetic gradient,
(ii) a highest first-moment m1 flow-spoiled dephasing magnetic gradient, and
(iii) at least one intermediate first-moment m1 flow-spoiled dephasing magnetic gradient, said intermediate first-moment m1 having a value that is between said lowest value and said highest value.

6. The method of claim 5, wherein:
said lowest first-moment m1 value is a base value whereat similarly valued MRI signals are expected to emanate from blood flowing in veins and from blood flowing in arteries; and
said highest first moment m1 value is a maximum value whereat substantial differences are expected to exist between MRI signals emanating from blood flowing in veins and MRI signals emanating from blood flowing in arteries.

7. The method of claim 6, wherein the value of at least one of said first-moment m1 flow-spoiled dephasing magnetic gradients is subject to operator control.

8. The method of claim 4, wherein said image data sets are acquired using electro-cardiac gating (ECG) and wherein:
said at least one BA image data set is taken at diastole,
said at least one hybrid $DA_x$ image data set is based on at least one of: (a) plural DA image data sets acquired using different respective first-moment m1 flow-spoiled dephasing magnetic gradients and (b) plural DA image data sets acquired at different phases of the cardiac cycle.

9. The method of claim 4, wherein generation of said hybrid image data set $DA_x$ comprises a pixel-by-pixel computation wherein, at each image pixel location:
(a) a difference between a DA data set pixel for a lowest first-moment and a DA data set pixel for an intermediate first-moment is compared to a threshold value;
(b) if the calculated difference is lower than said threshold, then the DA set pixel value for the highest first-moment is used in determining the hybrid $DA_x$ data set pixel value; and
(c) if the calculated difference is higher than said threshold, then the DA set pixel value for an intermediate first moment value is used in determining the hybrid $DA_x$ data set pixel value.

10. The method of claim 9, wherein said threshold value is subject to operator control.

11. The method of claim 1 wherein said different data acquisition imaging parameters comprise:
(a) a first moment m1 flow-spoiled dephasing magnetic gradient; and
(b) at least two different trigger delays to acquire data sets during respectively different phases of the cardiac cycle.

12. An MRI system configured to generate magnetic resonance images of fluid, said system comprising:
means for acquiring a plurality of N>2 image data sets for an imaged patient volume using respectively corresponding different data acquisition imaging parameters;
means for generating at least one hybrid image data set X for said imaged patient volume based on selective filling of a data set X pixel value at a particular location using pixel values at said particular location found in at least one of at least a subset of said plurality of image data sets; and
means for outputting an image data set that is based on said hybrid image data set X for storage or display as an image of said imaged patient volume.

13. The system of claim 12, wherein said image data set emphasizes MRI signals emanating from veins within said patient volume while de-emphasizing MRI signals emanating from arteries within said patient volume, thus providing a vein-optimized venography image.

14. The system of claim 12, wherein said image data set emphasizes MRI signals emanating from arteries within said patient volume while de-emphasizing MRI signals emanating from veins within said patient volume, thus providing an artery-optimized arteriographic image.

15. The system of claim 12, wherein:
at least one bright artery image data set BA is acquired for said patient volume;
at least one hybrid dark artery image data set $DA_x$ is generated for said patient volume based on at least a subset of plural of said acquired image data sets; and
an MRA subtraction image data set is generated by the difference between said BA and $DA_x$ data sets.

16. The system of claim 12, wherein said different data acquisition imaging parameters comprise:
(i) a lowest first-moment m1 flow-spoiled dephasing magnetic gradient,
(ii) a highest first-moment m1 flow-spoiled dephasing magnetic gradient, and
(iii) at least one intermediate first-moment m1 flow-spoiled dephasing magnetic gradient, said intermediate first-moment m1 having a value that is between said lowest value and said highest value.

17. The system of claim 16, wherein:
said lowest first-moment m1 value is a base value whereat similarly valued MRI signals are expected to emanate from blood flowing in veins and from blood flowing in arteries; and
said highest first moment m1 value is a maximum value whereat substantial differences are expected to exist between MRI signals emanating from blood flowing in veins and MRI signals emanating from blood flowing in arteries.

18. The system of claim 17, wherein the value of at least one of said first-moment m1 flow-spoiled dephasing magnetic gradients is subject to operator control.

19. The system of claim 15, wherein said image data sets are acquired using electro-cardiac gating (ECG) and wherein:
said BA image data set is taken at diastole,
said at least one hybrid $DA_x$ image data set is based on at least one of: (a) plural DA image data sets acquired using different respective first-moment m1 flow-spoiled dephasing magnetic gradients and (b) plural DA image data sets acquired at different phases of the cardiac cycle.

20. The system of claim 15, wherein generation of said hybrid image data set $DA_x$ comprises a pixel-by-pixel computation wherein, at each image pixel location:
   (a) a difference between a DA data set pixel for a lowest first-moment and a DA data set pixel for an intermediate first-moment is compared to a threshold value;
   (b) if the calculated difference is lower than said threshold, then the DA set pixel value for the highest first-moment is used in determining the hybrid $DA_x$ data set pixel value; and
   (c) if the calculated difference is higher than said threshold, then the DA set pixel value for an intermediate first moment value is used in determining the hybrid $DA_x$ data set pixel value.

21. The system of claim 20, wherein said threshold value is subject to operator control.

22. The system of claim 12 wherein said different data acquisition imaging parameters comprise:
   (a) a first moment m1 flow-spoiled dephasing magnetic gradient; and
   (b) at least two different trigger delays to acquire data sets during respectively different phases of the cardiac cycle.

* * * * *